(12) United States Patent
Lindstrom

(10) Patent No.: US 8,092,467 B1
(45) Date of Patent: Jan. 10, 2012

(54) APPARATUS AND METHOD FACILITATING REMOVAL OF A STRUCTURE IMPLANTED IN A BODY

(76) Inventor: Curtis Charles Lindstrom, Roseville, MN (US)

( * ) Notice: Subject to any disclaimer, the term of this patent is extended or adjusted under 35 U.S.C. 154(b) by 1380 days.

(21) Appl. No.: 11/584,264

(22) Filed: Oct. 20, 2006

Related U.S. Application Data

(60) Provisional application No. 60/731,599, filed on Oct. 28, 2005.

(51) Int. Cl.
*A61F 11/00* (2006.01)
(52) U.S. Cl. .................................................. 606/108
(58) Field of Classification Search .............. 606/191, 606/198, 108, 190, 129; 604/104, 107–109; 600/114; 81/442, 443, 128, 444–446; 294/93, 294/94
See application file for complete search history.

(56) References Cited

U.S. PATENT DOCUMENTS

| | | | |
|---|---|---|---|
| 4,574,800 A | 3/1986 | Peers-Trevarton | |
| 4,705,029 A * | 11/1987 | Borodulin et al. | 601/83 |
| 4,762,128 A * | 8/1988 | Rosenbluth | 606/192 |
| 4,943,289 A | 7/1990 | Goode | |
| 4,988,347 A | 1/1991 | Goode | |
| 5,011,482 A | 4/1991 | Goode | |
| 5,013,310 A | 5/1991 | Goode | |
| 5,081,985 A * | 1/1992 | Borodulin et al. | 601/1 |
| 5,207,683 A | 5/1993 | Goode | |
| 5,441,504 A * | 8/1995 | Pohndorf et al. | 606/129 |
| 5,549,615 A | 8/1996 | Hocherl | |
| 5,556,424 A | 9/1996 | Hocherl | |
| 5,632,749 A | 5/1997 | Goode | |
| 5,769,858 A | 6/1998 | Pearson | |
| 6,136,005 A | 10/2000 | Goode | |
| 6,167,315 A | 12/2000 | Coe | |
| 6,315,781 B1 | 11/2001 | Reinhardt | |
| 6,324,434 B2 | 11/2001 | Coe | |
| 6,358,256 B1 | 3/2002 | Reinhardt | |
| 6,687,548 B2 | 2/2004 | Goode | |
| 6,712,826 B2 | 3/2004 | Lui | |
| 6,772,014 B2 | 8/2004 | Coe | |
| 2002/0010475 A1 | 1/2002 | Lui | |
| 2004/0116939 A1 | 6/2004 | Goode | |

* cited by examiner

*Primary Examiner* — Gary Jackson
*Assistant Examiner* — Jonathan Hollm

(57) ABSTRACT

An apparatus and method facilitating removal, from a body, of an implanted elongated structure with a lumen such as a lead or catheter, comprises a plurality of wire stylets that are inserted together into the lumen and subsequently moved relative to each other in a longitudinal direction by manipulation at the proximal end. The stylets have dimensional features on their adjacent sides that mate together to minimize the overall diameter of the stylet assembly during insertion into the lumen. Interaction of the features on the stylets' adjacent sides, resulting from the subsequent relative displacement, causes the assembly to expand radially. The expansion is sufficient to engage the luminal surface of the implanted structure, thereby allowing traction forces to be applied, while minimizing deformation of the implanted structure. If repositioning of the apparatus is necessary, the stylets may be returned to initial relative positions, reestablishing a minimal overall diameter.

19 Claims, 12 Drawing Sheets

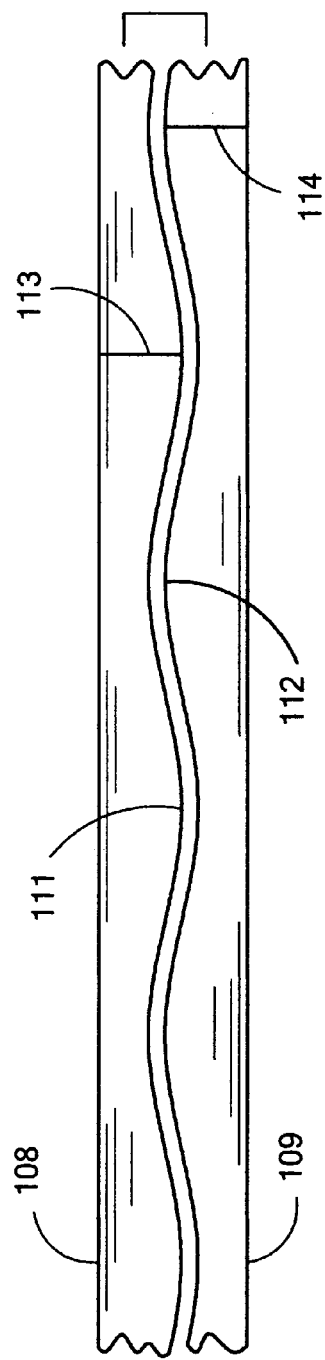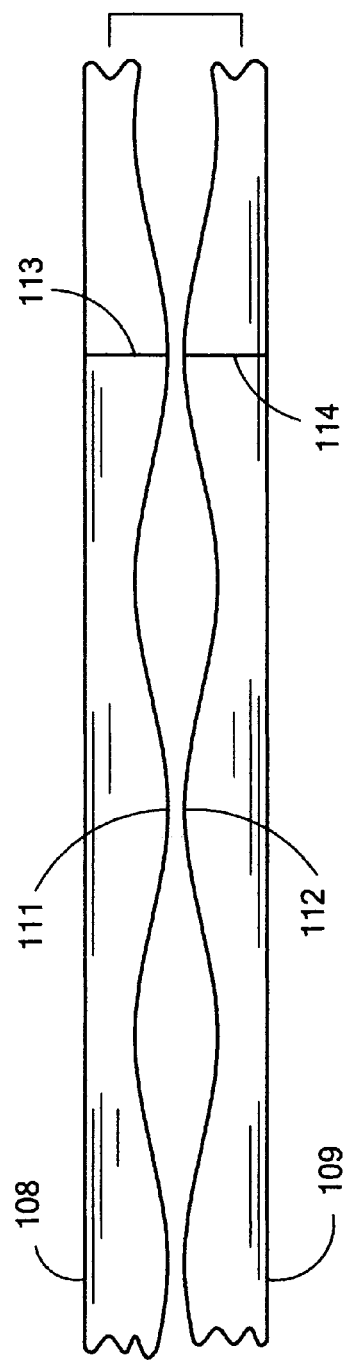

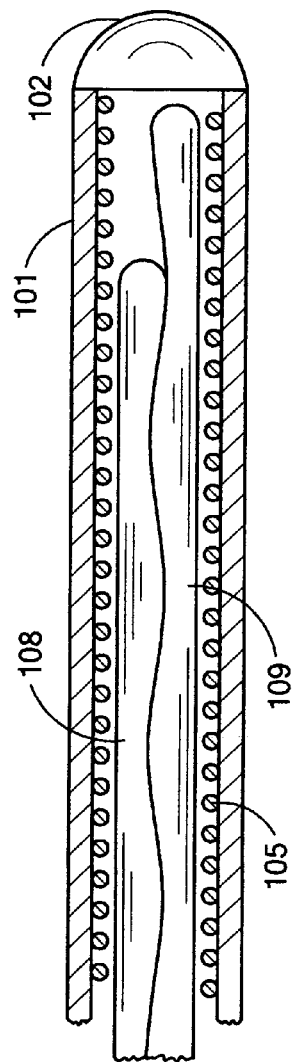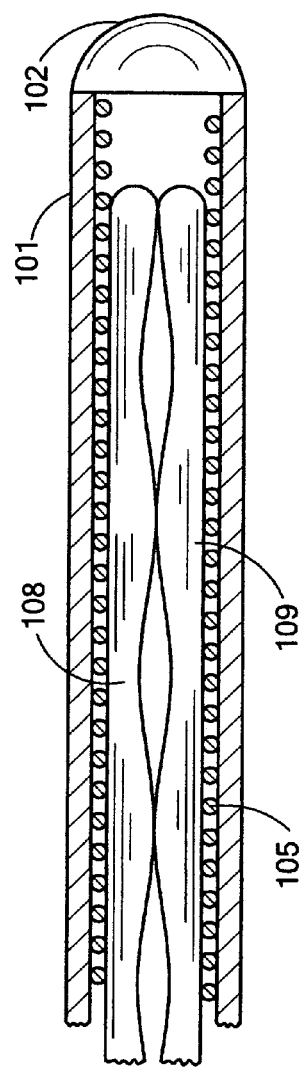

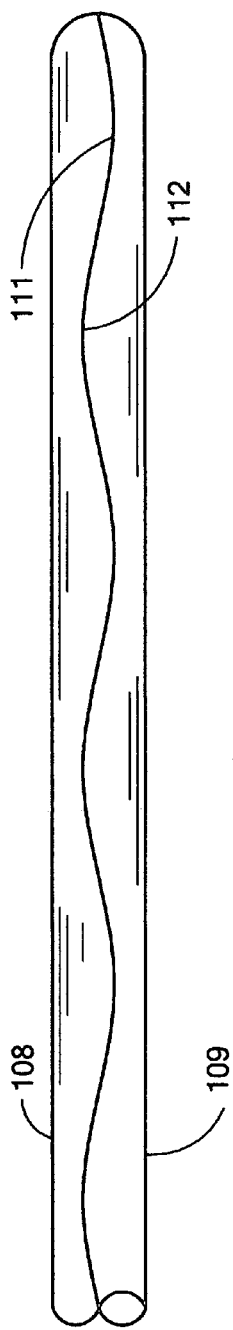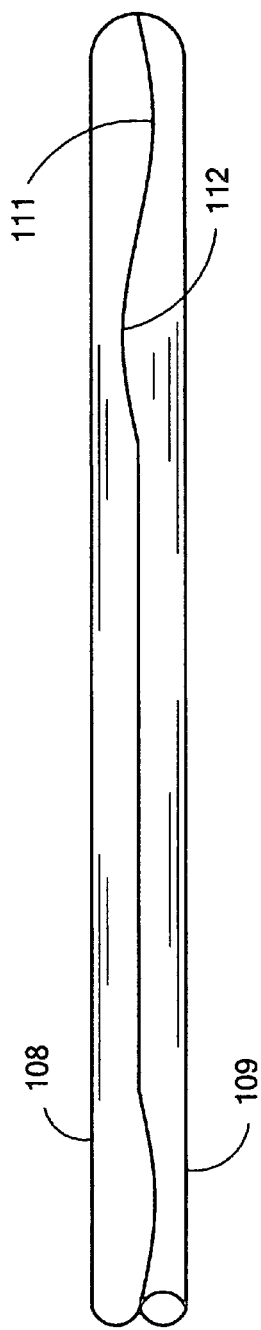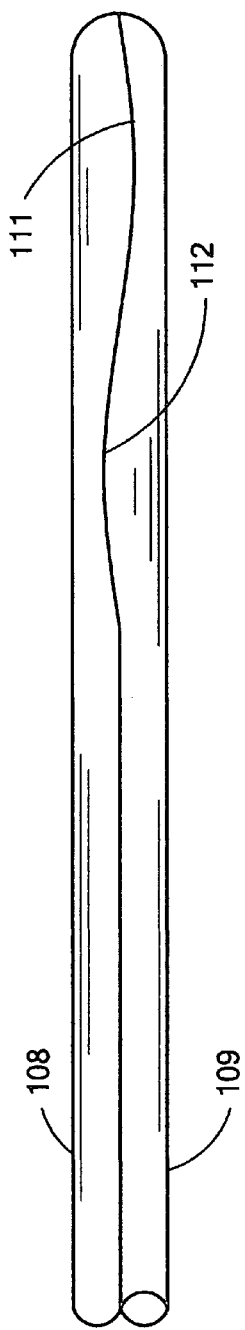

APPARATUS AND METHOD FACILITATING REMOVAL OF A STRUCTURE IMPLANTED IN A BODY

CROSS-REFERENCE TO RELATED APPLICATIONS

This application claims the benefit of Provisional Patent Application No. 60/731,599 entitled "Apparatus and Method for Removing a Structure Implanted in Biological Tissue," filed Oct. 28, 2005 by the present inventor.

FEDERALLY SPONSORED RESEARCH

Not Applicable

SEQUENCE LISTING OR PROGRAM

Not Applicable

BACKGROUND OF THE INVENTION

1. Field of Invention

This invention relates generally to elongated structures with an internal lumen such as pacemaker leads, defibrillator leads, and catheters, that are implanted transvenously or subcutaneously; it relates more specifically to apparatus and methods for removing such structures from a body.

2. Prior Art

Medical devices are chronically implanted to provide a variety of therapies to patients. Common examples are implantable pacemakers and defibrillators that monitor cardiac activity and deliver electrical therapy. Another example is an implantable drug pump that delivers pharmacological therapy. Because of the required size of such devices, they are usually placed subcutaneously or submuscularly in locations that maximize such factors as patient comfort and ease of implant. Monitoring and therapy usually occur at an anatomical location some distance from the device implant site, and this is routinely accomplished through the use of flexible elongated structures such as leads or catheters connected to the device. This arrangement has been widely accepted, in part, because leads and catheters allow for techniques such as transvenous introduction and minimally invasive subcutaneous tunneling, which are recognized for ease of use at implant and for limiting patient discomfort.

Transvenous pacemaker and defibrillator electrical leads typically are constructed with a flexible polymer body using materials such as silicone or polyurethane, with one or more internal lumens that extend the length of the lead. These lumens are used to place electrical conductors through the lead, allowing electrical connection between a medical device at the proximal end of the lead and the electrodes located at various positions along the lead and particularly at the distal end. At least one of these electrical conductors is typically a flexible multifilar coil that extends the length of the lead. The hollow center of the coil provides a pathway for temporary introduction of a wire stylet that aids in implanting the lead by providing stiffness and allowing shaping of the lead.

Although the expected life of an implanted transvenous lead is many years, removal is sometimes required due to mechanical or electrical failure, or changes in patient condition. Nonfunctional leads left in place can interfere with the placement and function of new leads, act as a conduit for infections, interfere with normal physiological functions such as cardiac valve function and compromise venous patency. Particularly for chronically implanted transvenous leads, removal can be difficult due to encapsulation or attachment of the surrounding tissue to the lead resulting from the natural physiological response to a foreign body. Removal is often made more difficult by design features of the lead that are intended to provide fixation, such as outwardly protruding tines at the distal portion of the lead or a helical screw at the distal end.

In some cases, extraction of a chronically implanted transvenous lead requires surgical removal; but often a lead can be successfully removed by the use of traction forces applied to the lead, or a combination of traction forces and excising sheaths that are advanced over the surface of the lead body. Because easy access is generally limited to the proximal end of the lead, these traction forces must be applied at or near the proximal end. A major problem with this method is that when extraction forces are applied, the flexible lead body and particularly the internal coil stretch. This results in a situation where traction forces are no longer effective for lead removal, and a situation which becomes increasingly dangerous as the structural integrity of the lead is increasingly compromised. The more damaged the lead becomes, the more likely the need for surgical removal becomes for the patient's safety.

Various methods have been employed to aid in lead removal. Early methods consisted of simple traction applied to the proximal end of the structure. More recent developments include excising sheaths that are advanced over the lead body and tools that employ laser excising methods, which have been described in numerous patents and publications.

In addition, special devices have been developed to facilitate lead extraction, which are introduced into the lumen of the lead and employ various methods to engage the coil and allow traction forces to be applied. Currently, several types of these extraction devices are commercially available from several companies, most notably Cook Medical, Spectranetics and VascoMed; and designs and methods are described in existing patents.

A series of related patents and published applications assigned to Cook Pacemaker Inc. and Cook Vascular Inc. by Goode et al. (U.S. Pat. Nos. 4,988,347; 4,943,289; 5,011,482; 5,013,310; 5,207,683; 5,632,749; 6,136,005; 6,687,548; U.S. Pub. No. 2004/0116939) and Lui (U.S. Pat. No. 6,712,826; U.S. Pub. No. 2002/0010475) describes various extraction devices. U.S. Pat. Nos. 4,988,347 and 5,013,310 describe an apparatus comprising a stylet wire with a wire coil wrapped around the distal end. Rotation of the stylet unwinds the wire coil and causes it to mesh with the coil of the lead. U.S. Pat. Nos. 4,943,289; 5,011,482; 5,207,683; 5,632,749; 6,136,005; 6,687,548; and 6,712,826 also describe a stylet wire with a wire coil wrapped around it that is unwound by rotation of the stylet wire. In addition, these patents describe embodiments that include: a flexible tube through which a fluid is passed to expand a balloon on the distal end; a flexible tube with strips cut in the distal end, which is expanded by means of an actuator rod inserted into the tube; a flexible tube with a series of barbs or a ridge, which is expanded by insertion of an actuator rod; a flexible tube with a slotted sleeve at the distal end, which is expanded by movement of an actuator rod; a flexible tube with an expandable sleeve of pliable material at the distal end, which is expanded by movement of an actuator rod; a flexible tube with a cylindrical rod at the distal end that is rotatable to an off-centered position; and a hollow tube with an extended projection at the distal end that is manipulated by insertion of a stylet. In addition, U.S. Pat. Nos. 6,136,005; 6,687,548; and 6,712,826 also describe a hollow tube and a stylet with a folded-back portion at the distal end or laterally flexible member attached to the distal end that acts as a hook to engage the lead coil. In addition, U.S. Pat. Nos. 6,687,548 and 6,712,826 and U.S. Publications 2004/0116939 and 2002/0010475 also describe a stylet pull wire with an expandable portion comprising multifilar helically wound or parallel wires that are compressed and expanded by advancement of an actuator portion such as a cannula or coiled wire.

A series of related patents assigned to Spectranetics Corp. by Coe et al. (U.S. Pat. Nos. 6,167,315; 6,324,434 B2; 6,772, 014 B2) describes various designs for extraction devices. U.S. Pat. Nos. 6,167,315 and 6,324,434 B2 describe a lead engaging member that is a sheath of elastic material or braided wires, which is held in a stretched or relaxed position by manipulation of a mandrel or concentric hypotubes. These patents also describe the use of a mandrel with an attached wire coil or helical ribbon that is expanded by manipulation of the mandrel. In addition, U.S. Pat. No. 6,772,014 describes a mandrel with expansion jaws that are controlled by manipulation of the mandrel, the use of a hypotube with a series of bristles that extend radially, and a mandrel with multiple radially expandable elastic members.

Patents assigned to VascoMed by Reinhardt et al. (U.S. Pat. Nos. 6,315,781 and 6,358,256) describe extraction devices. U.S. Pat. No. 6,315,781 describes a tube with an internal cable attached to an anchoring member at the distal end. Retraction of the cable results in distortion of the distal end of the cable and displacement of the anchoring member. U.S. Pat. No. 6,358,256 describes a slotted tube that is compressed and deformed radially by exerting a tensile force on an internal control wire.

Patents assigned to VascoMed by Hocherl et al. (U.S. Pat. Nos. 5,549,615 and 5,556,424) also describe extraction devices. U.S. Pat. No. 5,549,615 describes an extractor including an elongated hollow shell; a wire located within, which is movable relative to the shell; and an extractor head attached to the end of the wire. The extractor head includes barbs that spread out radially and hook the lead lumen when the wire is pulled. U.S. Pat. No. 5,556,424 describes an extractor consisting of a guide barrel, a beveled clamping element and a pull wire joined to the clamping element. The clamping element is moved by traction force on the pull wire, resulting in expansion of the extractor at the area of the clamping element.

U.S. Pat. No. 4,574,800 by Peers-Trevarton and assigned to Cordis describes a lead extractor designed to impart a wedging condition at the distal end of an implanted lead. The lead extractor comprises a tube with a slotted distal portion that is expanded by retracting a protrusion attached to a line contained within the tube.

U.S. Pat. No. 5,769,858 by Pearson et al. and assigned to Medtronic describes a locking stylet that is designed to impart a wedging condition at the distal end of an implanted lead. The locking stylet comprises a tubular member with a distal end that is deformed by use of a pull wire.

There are several limitations of the existing extraction systems described above. Stylets with wrapped wire coils require stylet rotation which can be difficult to control, and the coils may unwind during insertion and prematurely engage the lead. Conventional systems comprising hollow tubes with balloons, expandable wire mesh, hooks or expansion jaws, and systems with pull wire activated members, can be difficult to operate correctly, and are relatively complex and expensive to manufacture. In addition, conventional systems described above are often ineffective at engaging the implanted structure sufficiently to allow the required traction. These systems result in traction forces being applied unevenly along the lead, limiting the effectiveness for lead removal, with most existing systems engaging the implanted structure only at the distal end or at one other location. While providing a means of engaging the implanted structure, these conventional systems do little to reinforce or stabilize the overall structure during application of the traction forces. Another limitation of conventional systems is that once the locking mechanism has been engaged, which often involves permanent deformation of a part, it is difficult or not possible to disengage it. This makes repositioning or removal of the extraction system difficult if it becomes necessary due to complications, potentially resulting in the need for surgical intervention.

Although it is not as common as transvenous implantation, implantable pacemaker and defibrillator leads are also implanted through tunneling techniques in subcutaneous and epicardial locations. Leads for this type of implant are similar in construction to transvenous leads with internal lumens as described above. As is true for transvenous leads, removal of leads from these locations is sometimes also necessary due to mechanical and electrical malfunction. Although the consequences of leaving abandoned leads in these locations are generally less of a concern than for transvenous leads, they are often removed for patient comfort, to eliminate or prevent infection and to eliminate interaction with other implanted devices. Conventional extraction of these leads with traction is subject to the same problems explained above for transvenous leads, and surgical removal carries similar undesirable risks of morbidity and patient discomfort.

Implantable drug pumps may also make use of chronically implanted flexible leads or catheters constructed with a hollow lumen, for physiological monitoring and for drug delivery to specific locations in the body that are remote from the device implant site. As with pacemaker and defibrillator leads, conventional extraction of these electrical leads and catheters with traction is subject to the same problems explained above, and surgical removal carries similar undesirable risks of morbidity and patient discomfort.

From the foregoing discussion, those skilled in the art will appreciate that a need exists for a means to facilitate extraction of chronically implanted leads and catheters that will obviate the cited drawbacks of those currently available. The invention of this disclosure provides such benefits with an apparatus and method of use that overcome the limitations of existing extraction devices mentioned above.

SUMMARY OF THE INVENTION

The present invention is an apparatus and method of use that facilitate removal, from a body, of an implanted elongated structure that has an internal lumen, such as an endocardial or subcutaneous cardiac pacemaker or defibrillator lead, or catheter. The apparatus is an assembly comprising 2 or more wire stylets that are inserted together into the lumen of the implanted structure and which are subsequently moved relative to each other in a longitudinal direction by manipulation at the proximal end. The stylets have dimensional features on their adjacent sides that mate together to minimize the overall diameter of the assembly during insertion into the lumen. Interaction of the features on the adjacent sides of the stylets, resulting from the subsequent relative displacement, causes the assembly to expand radially. The expansion is sufficient to engage the luminal surface of the implanted structure, thereby allowing necessary traction forces to be applied at the proximal end of the apparatus and implanted structure during the extraction process, while minimizing distortion or elongation of the implanted structure. If repositioning or removal of the apparatus if necessary, the stylets may be returned to initial positions relative to each other, reestablishing a minimal overall diameter.

In a preferred embodiment, the assembly comprises 2 wire stylets. The concept of the assembly and method of use may be readily expanded to include an assembly of 3 or more similar stylets. However, it should be apparent that the complexity associated with more than 2 stylets increases the difficulty of manufacture and usage. Because the typical diameter of the coil lumen in conventional leads is small, the number of stylets comprising the assembly is also limited by material properties and limitations of machining technology.

In the past, the manufacture of stylets with small dimensional details has been limited by available technology. However, currently available precision machining technology allows for producing features of small dimensions on stylets such as those described below.

In a preferred embodiment, the dimensional features of the stylets have a rounded or sinusoidal profile. However, in alternative embodiments the features may have a different profile with curved edges such as an asymmetrical or damped sinusoid, or straight edges such as a sawtooth shape.

Variations also exist as to the placement of the dimensional features of the stylets. In a preferred embodiment, the features are located along substantially the entire lengths of the stylets. In alternative embodiments the features may be located only periodically along the lengths, or may be located only at one location such as at the distal ends of the stylets.

Radial expansion of the assembly requires only a short distance of longitudinal displacement of the stylets relative to each other, the extent of which is determined by the size and shape of the dimensional features. The relative displacement may be achieved, for example in a preferred embodiment comprising 2 stylets, by moving the stylets in opposite longitudinal directions or by moving one stylet while holding the other in a fixed position. The relative movement may be effected by grasping the stylets directly or preferably by means of a control mechanism attached to the proximal end of the stylet assembly. In a preferred embodiment, the control mechanism provides a means to grasp the stylet assembly during insertion of the stylets into the lumen of the implanted structure and during application of traction forces. The mechanism also provides a means to control the relative longitudinal movement of the stylets of the assembly. The mechanism may be removable, or a permanent part of the assembly. The action of the control mechanism may, for example, be controlled simply by manual pressure, or alternatively by a lever or a screw mechanism.

As an illustration of the method of use, an example lead extraction procedure would proceed as follows. The proximal end of the implanted lead to be removed is first exposed by common surgical techniques. The terminal pin and any excess lead at the proximal end may be cut off, and a coil expander may be used to improve access for the stylet assembly. The extraction stylet assembly, while in a position of minimal diameter, is introduced into the lumen of the coil and advanced to the desired depth, typically to the distal end of the structure's lumen. By means of the control mechanism at the proximal end of the apparatus, the stylets are moved relative to each other to an expanded position. Traction forces are applied to the proximal end of the implanted structure and the apparatus until the implanted structure is removed. If traction forces alone are not sufficient to remove the implanted structure, excising sheaths are advanced over the structure as traction forces are applied. If it is necessary to reposition the stylet assembly, the control mechanism is used to move the stylets relative to each other to a position where a minimum diameter is reestablished. This disengages the assembly from the lumen of the structure. The stylet assembly is then advanced or retracted to the desired location. The control mechanism is again used to move the stylets of the assembly to an expanded position as before, and traction forces are reapplied. If difficulty is encountered at any time, the control mechanism may be used to move the stylets to a position of minimum diameter, which disengages the assembly from the lumen and allows the assembly to be removed from the implanted structure.

The various embodiments and method of use of the present invention described above provide an effective means for removal of an implanted structure that overcomes the limitations of existing extraction devices described previously. The present invention does not rely on relatively complex systems such as hollow tubes or pull wires with hooks, wire mesh, or mechanical expansion jaws, or permanently deformed parts, that are incorporated in conventional systems. The present invention does not rely on hooking or snagging the coil like conventional systems, which result in application of traction forces to primarily the coil, and at one location. Instead, the present invention engages the implanted structure by applying a radial expansion force, at a selected location; or in a preferred embodiment, by applying a uniform expansion force along substantially the length of the apparatus. This method of engagement forces the coil and lead body together, inhibiting separation of the coil from the lead body, and thereby serves to reinforce and stabilize the implanted structure while traction forces are applied. This also allows the traction force to be applied to both the implanted structure and the extraction apparatus together. In addition, the present invention provides a means for releasing the engagement force and removal of the apparatus should it become necessary due to complications, overcoming a limitation of conventional systems that are difficult or not possible to disengage.

The summary given above is not intended to describe all variations for the present invention. A more complete understanding will be evident from the following detailed description and drawings.

DESCRIPTION OF THE DRAWINGS

FIG. 3 is a side view of a portion of the stylet assembly of FIG. 2A constructed in accordance with one embodiment of the present invention, when in a position of minimum radial expansion.

FIG. 4 is a side view of a portion of the stylet assembly of FIG. 2A constructed in accordance with one embodiment of the present invention, when in a position of maximum radial expansion.

FIG. 5 is a partial cross-sectional side view of the distal portion of a lead with the stylet assembly inserted and in a position of minimum radial expansion.

FIG. 6 is a partial cross-sectional side view of the distal portion of a lead with the stylet assembly inserted and in a position of maximum radial expansion.

FIG. 9 is a side view of a portion of the stylet assembly constructed in accordance with one embodiment of the present invention, illustrating dimensional features that are located continuously along the length of the stylets.

FIG. 10 is a side view of a portion of the stylet assembly constructed in accordance with one embodiment of the present invention, illustrating dimensional features that are located periodically along the length of the stylets.

FIG. 11 is a side view of a portion of the stylet assembly constructed in accordance with one embodiment of the present invention, illustrating dimensional features that are located only at the distal portion of the stylets.

DESCRIPTION OF THE EMBODIMENTS

In the following detailed description of the embodiments, reference is made to the accompanying drawings which form a part hereof, and which illustrate embodiments in which the invention may be practiced. It is understood that the description is intended to be illustrative, and not restrictive. Other embodiments may be utilized and structural and functional changes may be made without departing from the scope of the present invention.

The following explanations use a simple unipolar pacemaker lead with a central lumen as an example of an implanted structure to be removed from a body, for illustrative purposes. These explanations apply equally well for more complex bipolar, tripolar and quadripolar pacemaker and defibrillator leads that have several electrodes along the lead body, and several electrical conductors that run coaxially or through multiple lumens in the lead body. If access exists to multiple lumens in a lead body, multiple stylet assemblies could be used simultaneously to facilitate the extraction process. In addition, these explanations apply to leads that are implanted transvenously or subcutaneously.

Figure 1:
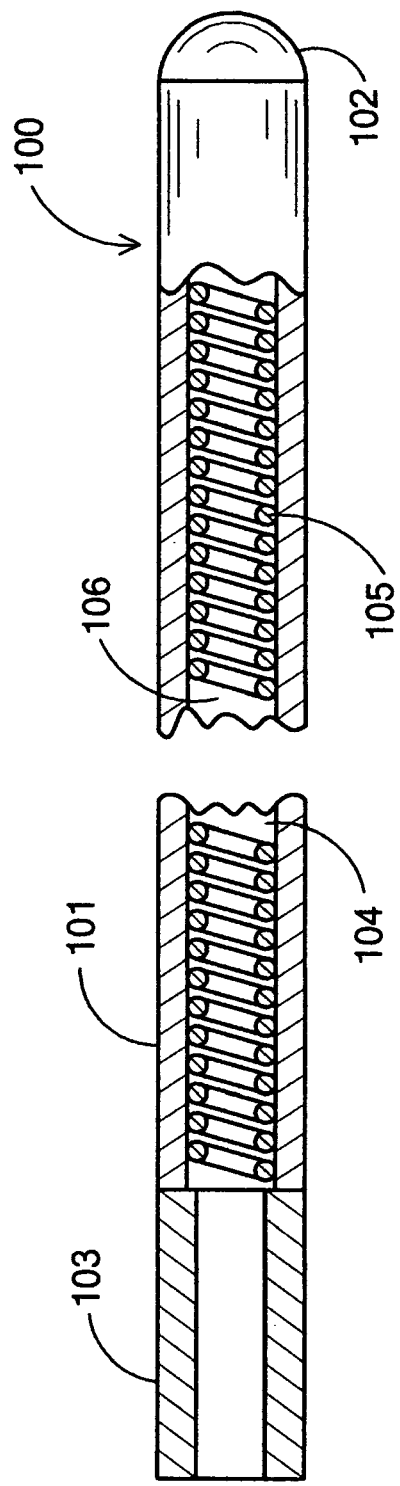
FIG. 1 is a partial cross-sectional side view that shows relevant major components of a unipolar transvenous pacemaker lead, included for reference and indicated as prior art.

FIG. 1 shows a partial cross-sectional side view of a portion of a unipolar transvenous pacemaker lead 100, included for reference. Typical pacemaker and defibrillator leads are between 1.5 and 3.0 mm in diameter, and between 40 and 100 cm in overall length to accommodate variations in patient size and implant location. Because of the dimensions, it is not possible to show the entire lead and necessary details in the same figure. Therefore, FIG. 1 provides an expanded view of a portion to show relevant major components. Electrode 102 on the distal end of lead 100 is used to provide electrical stimulation to the surrounding tissue and to sense biological electrical activity. Terminal pin 103 on the proximal end of lead 100 is used to connect lead 100 to an implanted pulse generator. The body 101 of lead 100 has an internal lumen 104 that extends from the proximal end to the distal end of the lead body. Lumen 104 provides a conduit for metal coil 105, which extends the length of the lead and is used to electrically connect distal electrode 102 with proximal terminal pin 103. Lead body 101 is constructed of a flexible biocompatible material such as silicone, polyurethane or other suitable polymer. Coil 105 is made of a metal wire with appropriate electrical and mechanical properties and is typically wound multifilar. The wire of coil 105 is typically covered with an electrically insulative coating such as polyurethane or polytetrafluorethylene (PTFE). Coil 105 has a hollow center 106 that provides a pathway for temporary introduction of a metal stylet wire. Stylet wires are used to aid in placing the lead, by providing stiffness and allowing shaping of the lead. Stylets are also used to aid in extraction of the lead, if necessary, by providing a means to engage the lead to allow application of traction forces. Lead 100 is introduced into a vein and advanced into the heart, with the distal electrode 102 typically placed in the right atrium or right ventricle of the heart. Alternatively, lead 100 is introduced into a subcutaneous or epicardial space using tunneling techniques and blunt dissection.

Figure 2A:
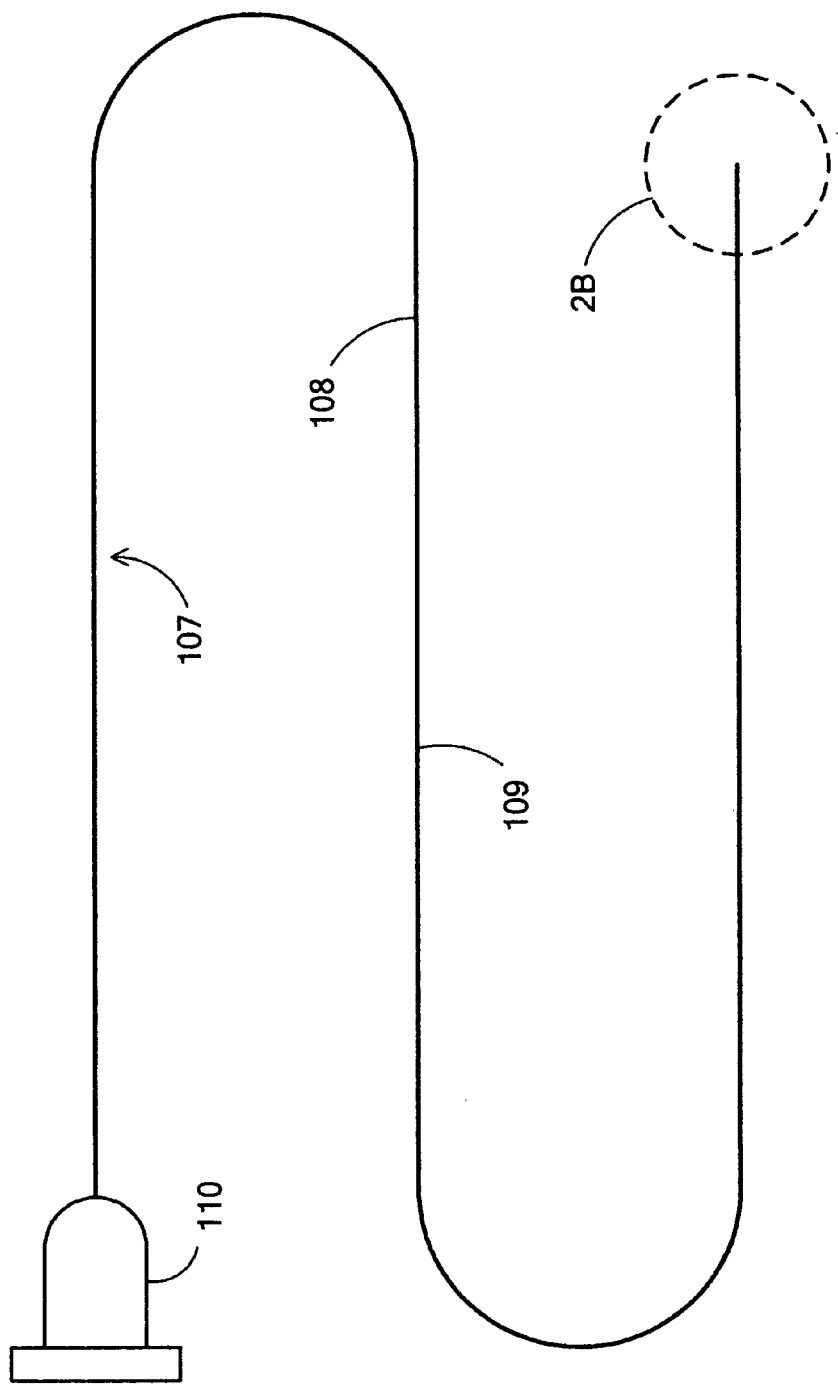
FIG. 2A is a side view of a preferred embodiment of the invention of this disclosure, an apparatus that is used to facilitate removal of an implanted structure such as the lead shown in FIG. 1.
Figure 2B:
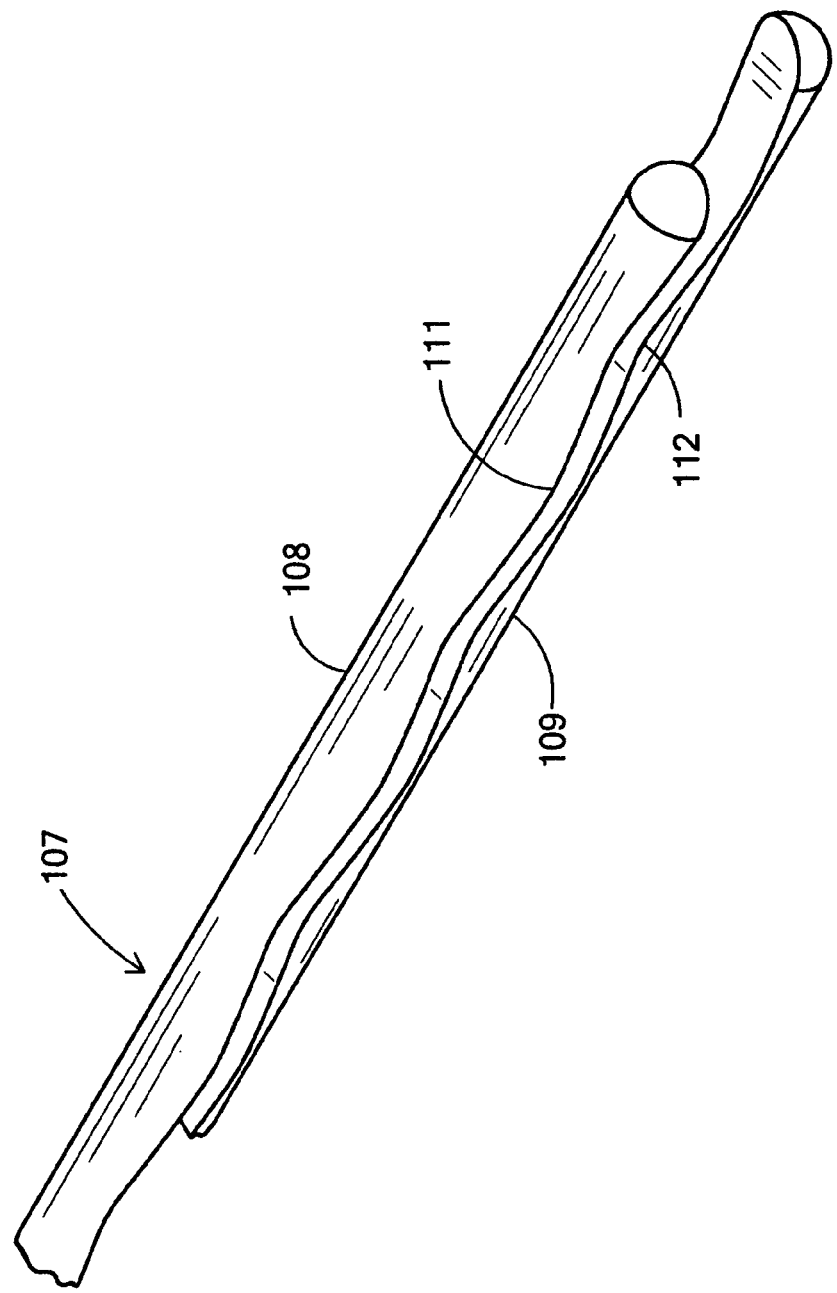
FIG. 2B is an expanded perspective view of the distal portion of the apparatus shown in FIG. 2A.

FIG. 2A is a side view of a preferred embodiment of the invention of this disclosure, an apparatus 107 that is used to facilitate removal of an implanted structure such as lead 100. In this embodiment, apparatus 107 comprises 2 similar wire stylets 108 and 109, together referred to as a stylet assembly, and a control mechanism 110 at the proximal end. Stylets 108 and 109 are made of a metal with appropriate mechanical properties such as stainless steel. Control mechanism 110 provides a means for grasping the assembly and for controlling the relative longitudinal positions of stylets 108 and 109. The stylets may be provided in various lengths to correspond with the length of the lead to be removed and ideally are slightly longer than the lead. Because of the dimensions, it is not possible to show the entire apparatus and the important details in the same figure. The overall length of the apparatus may typically be 50 to 110 cm, while the diameter of the stylets may typically be less than 1 mm. Therefore, details are shown in FIG. 2B, which is an expanded perspective view of the distal portion of the apparatus of FIG. 2A showing separate stylets 108 and 109, and dimensional features 111 and 112 on their respective adjacent sides.

Although the stylets would normally be in contact on their adjacent sides, in some of the figures they are shown separated by a small distance, for clarity. FIG. 3 is a side view of a portion of the stylet assembly of FIG. 2A. Stylets 108 and 109 have dimensional features 111 and 112 on their respective adjacent sides that interact to change the overall radial dimension of the stylet assembly as the relative longitudinal positions of stylets 108 and 109 are changed. Dimensional features 111 on stylet 108 and 112 on stylet 109 mate together, to minimize the diameter of the stylet assembly when the stylets are in one position relative to one another, shown in FIG. 3 and herein referred to as the closed position. Stylets 108 and 109 are cylindrical on their outer surfaces; and the assembly, when in the closed position, is approximately the shape and size of coil lumen 106 but is small enough to allow easy insertion into the coil lumen. The radial dimension, or depth, of the features 111 and 112 is large enough to provide for sufficient expansion of the assembly for fixation, but small enough to retain adequate mechanical strength of the stylets. Features such as those described herein may, for example, be produced on wire stylets by currently available machining technology. In a preferred embodiment, the diameter of the assembly and the depth of the features are appropriately tailored to provide fixation for a range of lumen sizes. In an alternative embodiment the assembly may be tailored to fit a specific lumen size.

FIG. 4 is a side view of a portion of the stylet assembly shown in FIG. 3, after a change in the relative longitudinal positions of the stylets. As a result of relative longitudinal displacement, interaction of features 111 and 112 on the adjacent sides of stylets 108 and 109 causes the assembly to expand radially. These positions are referred to herein as expanded positions. The expansion continues up to the position of maximum expansion shown in FIG. 4. The radial dimension of the stylet assembly, when in an expanded position, is large enough for the stylets to engage the luminal surface of coil 105 sufficiently to allow traction forces to be applied during the lead extraction process. Markings 113 and 114, on the outer surfaces at the proximal portion of the stylets, may be provided to indicate the distance of stylet relative movement and therefore the amount of expansion.

The following description summarizes the method of use of the apparatus described above. The stylet assembly comprising stylets 108 and 109 is initially in the closed position shown in FIG. 3. The distal end of the stylet assembly is first inserted into the proximal end of lead 100 and advanced through lumen 106 of coil 105 to the distal end of lead body 101, as indicated in FIG. 5, or other desired intermediate position. When the assembly has been advanced to the desired position, control mechanism 110 is used to effect relative longitudinal movement of stylets 108 and 109. This results in an expanded position of the assembly, as shown in FIG. 6, that is sufficient to engage the luminal surface of coil 105 with enough force to allow traction forces to be applied to the apparatus and lead. Traction forces are then applied to the proximal end of the implanted structure and the apparatus until the implanted structure is removed. If traction forces alone are not sufficient to remove the implanted structure, excising sheaths are advanced over the structure as traction forces are applied until the implanted structure is removed. If it is necessary to remove or reposition the stylet assembly, control mechanism 110 is used to return the assembly to the closed position, which releases the engaging force.

Figure 7:
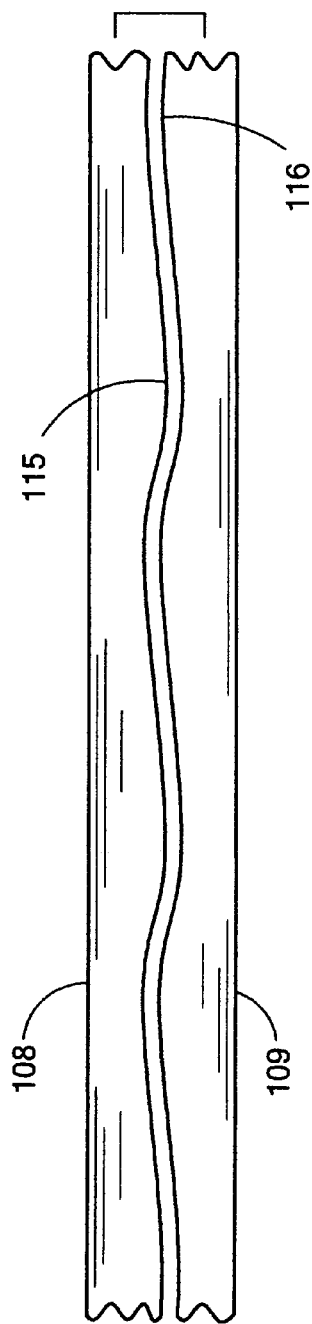
FIG. 7 is a side view of a portion of the stylet assembly constructed in accordance with one embodiment of the present invention, where the dimensional features of the stylets have a rounded but asymmetrical profile similar to a damped sinusoid.
Figure 8:
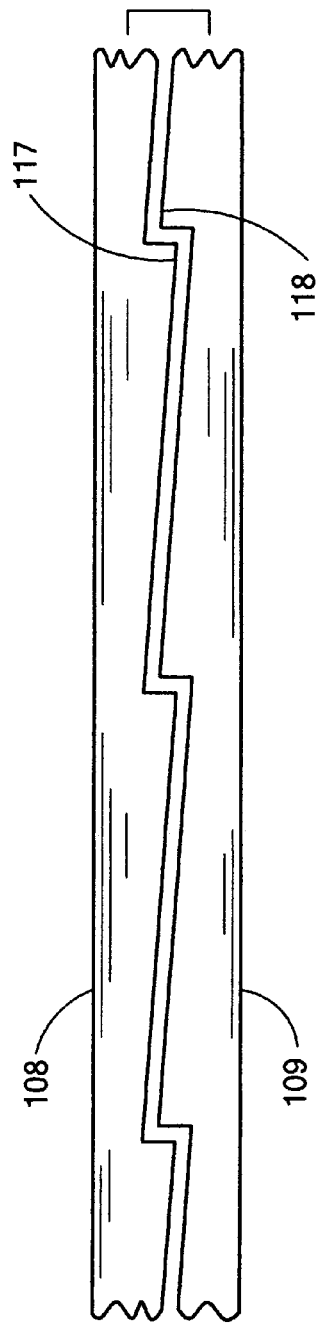
FIG. 8 is a side view of a portion of the stylet assembly constructed in accordance with one embodiment of the present invention, where the dimensional features of the stylets have a linear profile similar to a sawtooth shape.

In the previous FIGS. 2B through 6, the dimensional features of the stylets have been shown as having a rounded, sinusoidal shape. However, other shapes may also be used with similar results and without departing from the scope of the invention. FIGS. 7 and 8 are side views of portions of stylet assemblies comprising 2 stylets, with alternative shapes of the dimensional features along the length of the stylets. These, and the previous examples, all have the advantage of providing variable radial expansion. The variations shown by example in FIGS. 7 and 8 are representative of additional embodiments, but the scope of this invention is not limited to these shapes.

FIG. 7 is a side view of a portion of the stylet assembly where dimensional features 115 and 116 of stylets 108 and 109 respectively, have a rounded but asymmetrical profile, similar to a damped sinusoid, in order to change characteristics related to the relative movement of the stylets. This profile provides for a slower expansion in one direction and a more rapid expansion in the other.

FIG. 8 is a side view of a portion of the stylet assembly where dimensional features 117 and 118 of stylets 108 and 109 respectively, have a linear profile similar to a sawtooth shape.

In the previous FIGS. 2B through 8, dimensional features of the stylets have been shown as located continuously along the length of the stylets. In additional embodiments, the location of the features may be varied, for a more even distribution of the forces provided by the expansion of the assembly to engage the luminal surface of the coil; or to limit or concentrate those forces at a particular location or locations.

In some cases it may be advantageous to include dimensional features as shown in FIG. 9, a side view of a portion of the stylet assembly, where features 111 and 112 of stylets 108 and 109 are located continuously along the lengths of the stylets. Advantages of this distribution of the features are that it results in a greater overall engaging force and a more even distribution of the force provided by the stylet expansion to engage the luminal surface of the coil.

Alternatively, in some cases it may advantageous to limit the number of dimensional features in order to decrease friction between stylets 108 and 109 during relative longitudinal movement of the stylets. FIG. 10 is a side view of a portion of the stylet assembly where features 111 and 112 are located only periodically along the lengths of the stylets.

In some cases, in addition to limiting friction between stylets it may be advantageous to expand the assembly and apply radial forces to engage the coil only at a specific location, particularly at the distal end of the stylets. FIG. 11 is a side view of a portion of the stylet assembly where features 111 and 112 of stylets 108 and 109 are located only at the distal portion rather than continuously or periodically along the lengths of the stylets.

In the embodiments shown in FIGS. 9, 10 and 11, the stylets are shown as being the same length when in the initial closed position. In some cases it may be advantageous to make one stylet longer than the other when in the initial closed position, as shown previously in FIGS. 2B, 5 and 6. This arrangement in FIGS. 2B, 5 and 6 allows the shorter stylet to move distally during expansion of the assembly, allowing expansion at the very distal end of the lead.

Figure 12:
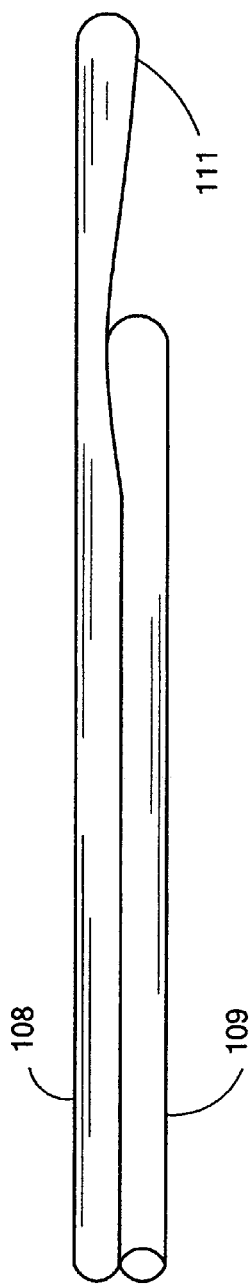
FIG. 12 is a side view of a portion of the stylet assembly constructed in accordance with one embodiment of the present invention, where the distal end of one stylet is longer than the other during insertion into the lead, to provide expansion at the distal end.

FIG. 12 is a side view of a portion of the stylet assembly in an additional embodiment where stylet 108 is longer than stylet 109 in the initial closed position, and with dimensional features located only at the distal end. This combination allows for selective application of extraction forces at a primary location of lead fixation in the case of tined leads or leads that incorporate a helical screw for fixation. An additional benefit of this embodiment is the potential to allow for application of torque selectively at the distal end, to remove a helical fixation screw.

Figure 13:
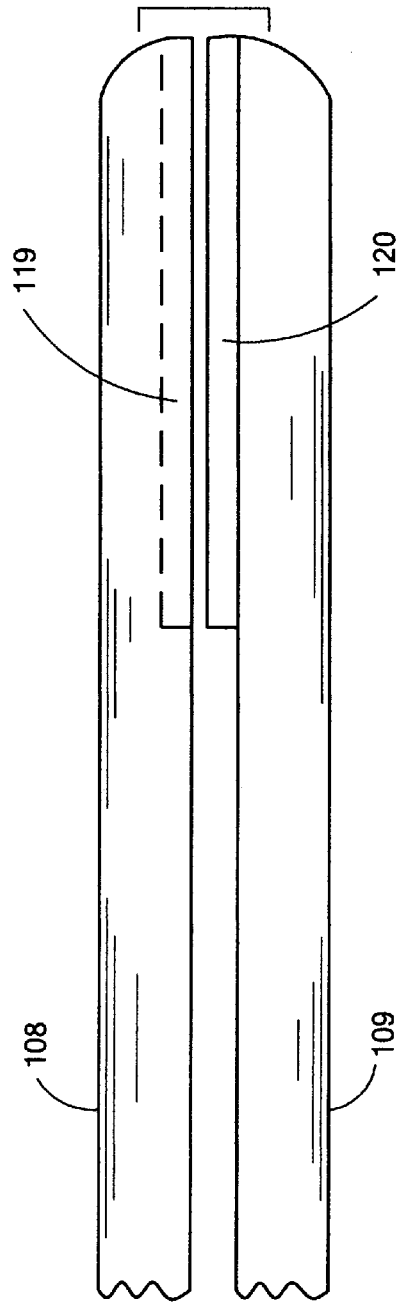
FIG. 13 is a side view of the distal portion of the stylet assembly constructed in accordance with one embodiment of the present invention, where the dimensional features of the stylets are an angled ridge and corresponding channel that cause expansion of the stylet assembly in a direction parallel to the plane between the stylets.
Figure 14:
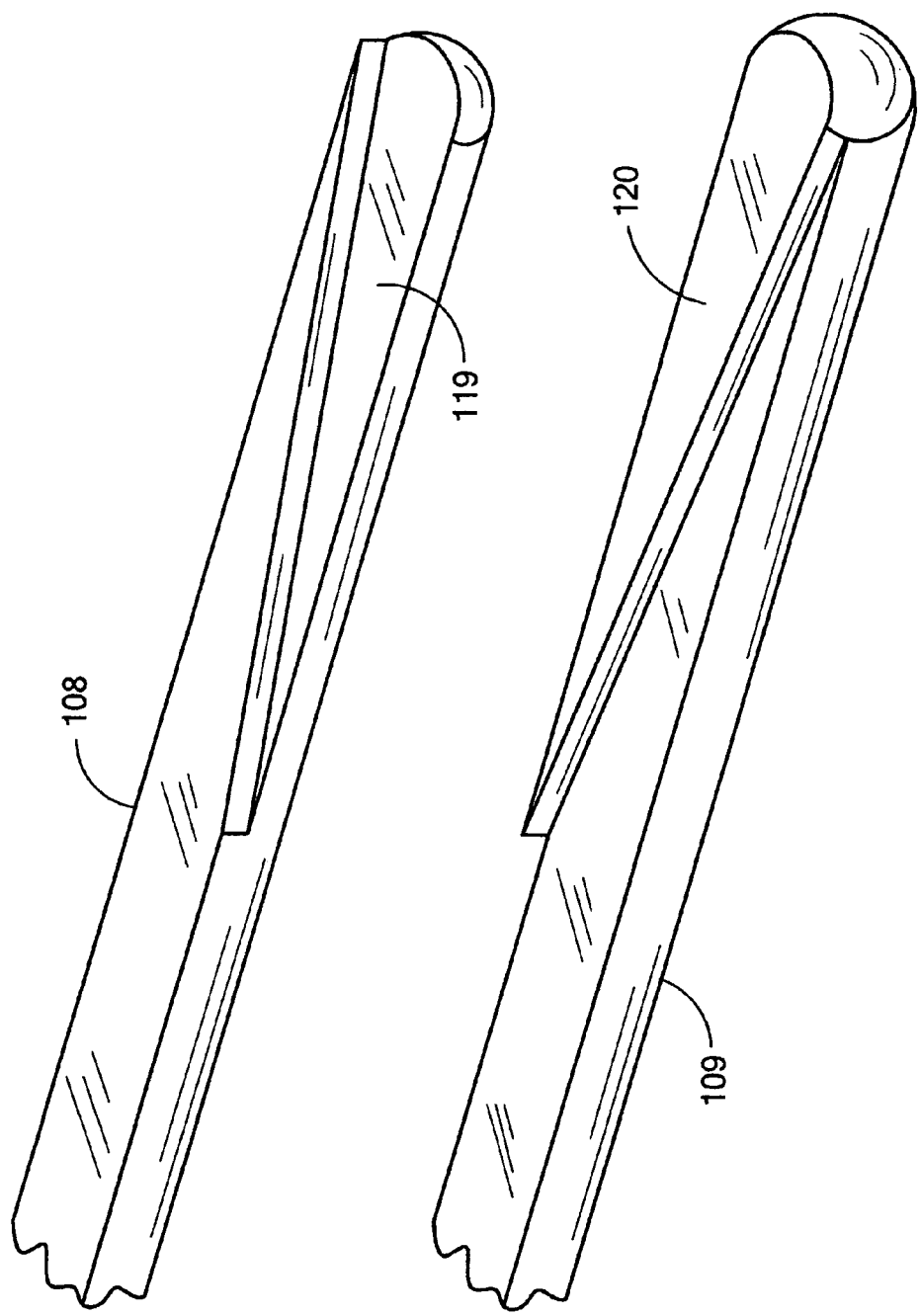
FIG. 14 is a perspective view of the distal portion of the stylets shown in FIG. 13.

The above examples utilize dimensional features, referred to herein as perpendicular features, which cause the assembly to expand in a direction perpendicular to the plane between the 2 stylets. Alternatively, the stylets may utilize dimensional features, referred to herein as parallel features, which cause the assembly to expand in a direction parallel to the plane between the 2 stylets. FIGS. 13 and 14 are side and perspective views respectively, of a portion of stylets 108 and 109 that show features that are an angled ridge 120 and corresponding channel 119. Note that in FIG. 14, stylet 108 is rotated to better illustrate the features of the normally adjacent sides. In this embodiment, relative longitudinal movement of stylets 108 and 109 causes radial expansion parallel to the plane between the stylets. Parallel features may be located continuously, periodically, or only at specific locations along the stylets, for the same reasons that are explained above for the features that cause perpendicular expansion.

A further embodiment of the stylet assembly includes features that cause expansion in both directions by utilizing a combination of the perpendicular and parallel features explained above.

Figure 15:
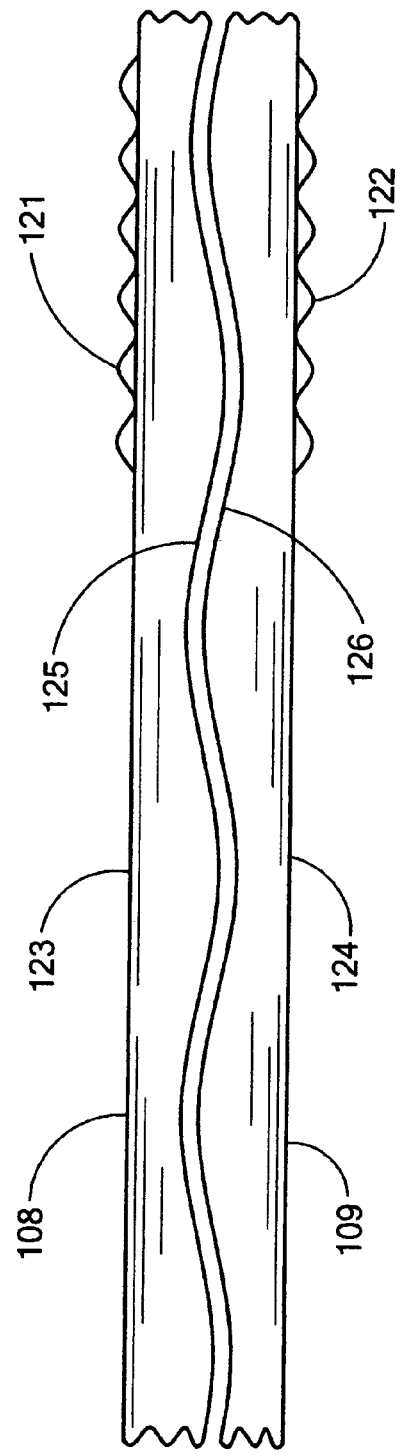
FIG. 15 is a side view of a portion of the stylet assembly of the present invention illustrating the locations of various enhancements on the inner and outer surfaces of the stylets that provide additional frictional forces, lubrication and temporary adhesion between the stylets.

In some cases it may be advantageous to provide additional frictional force between the stylet assembly and the inner surface of coil 105 when the assembly is expanded for application of traction forces. This can be accomplished by providing a textured or rough outer surface on stylets 108 and 109, or by providing small dimensional features on the outer surfaces such as barbs or ridges that are designed to fit the between the windings of coil 105. FIG. 15 is a side view of a portion of the stylet assembly indicating locations 121 and 122 of these surface features.

In order to facilitate advancement of the stylet assembly into the lead, a lubricious coating may be provided on the outer surface of the assembly. Locations 123 and 124 of FIG. 15 indicate where a lubricious coating may be provided on the outer surfaces of stylets 108 and 109 to aid in insertion. This coating may be in the form of a viscous liquid such as mineral oil, or a solid coating such as polytetrafluorethylene (PTFE). The coating may be provided over the entire outer surface or limited to selected regions of the assembly.

In addition, in some cases it may be advantageous to provide a lubricious coating at locations 125 and 126 on the adjacent sides of stylets 108 and 109 to facilitate oppositional longitudinal movement of the stylets. As with the coating on the outer surface of the assembly described above, this coating may be in the form of a viscous liquid such as mineral oil, or a solid coating such as PTFE, and may be provided over the entire adjacent surfaces or limited to selected regions of the assembly. As in previous figures, in FIG. 15 the 2 stylets are shown slightly separated in order to indicate locations more clearly.

In some embodiments it may be advantageous to provide temporary adhesion between stylets 108 and 109 during insertion of the assembly into the lead. Locations 125 and 126 also indicate where a coating may be provided on the adjacent surfaces of stylets 108 and 109 to provide temporary adhesion between the stylets. This coating may be a viscous fluid such as mineral oil, which also provides lubrication as described above, or a solid coating with a low breaking strength such as mannitol. A suitable solid coating is one that is sufficient to hold the stylets together during introduction into the lead, but one that would easily separate when the operator initiates relative longitudinal movement of the stylets. This adhesive coating may be provided over the entire adjacent surfaces of the stylets or limited to selected regions of the assembly.

Figure 16:
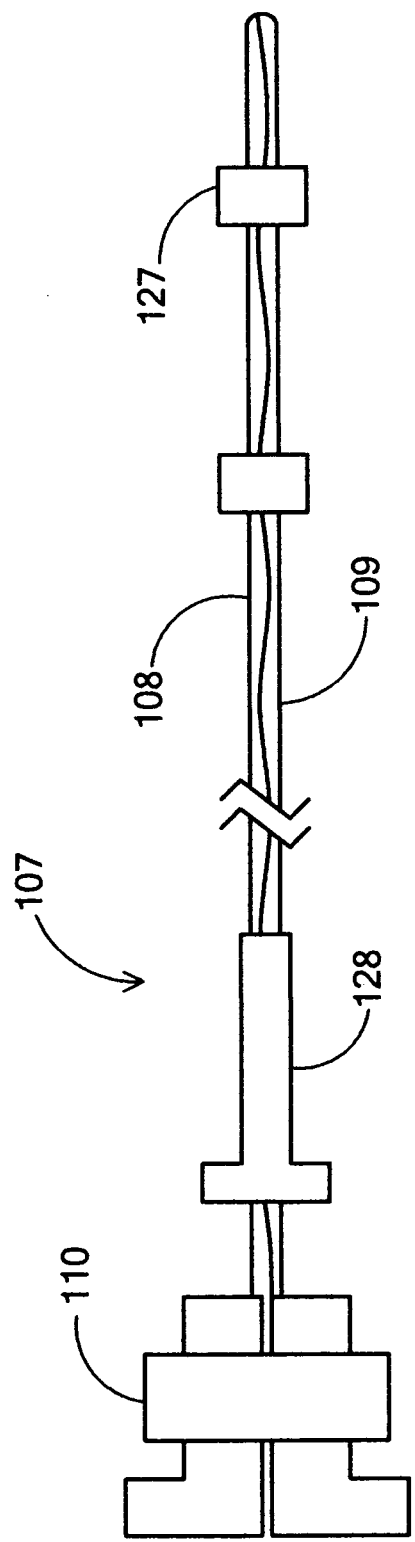
FIG. 16 is a side view of the present invention including a series of movable rings and a removable sheath surrounding portions of the stylet assembly, which serve to temporarily maintain the relative positions of the stylets.

Another method for temporarily maintaining the relative position of the stylets of the assembly, before and during insertion into the lead, is provided by the inclusion of movable rings or sheaths around the stylet assembly. These may be moved proximally over the assembly as it is advanced into the lead, or may be removable by breaking or splitting as is commonly done with lead introducers. A single splittable sheath could cover the majority of the length of the assembly or several shorter lengths could be used to cover smaller sections. FIG. 16 is a partial side view of apparatus 107 showing examples of both sliding rings 127 and a splittable sheath 128 that serve to temporarily maintain the relative position of stylets 108 and 109. Because the stylets are very long compared to their width, this side view is broken in length in order to enlarge and better illustrate the components.

These enhancements described above for lubrication, for temporary adhesion of adjacent surfaces and for temporarily maintaining the relative position of the stylets, are not exclusive and may be used in various combinations within the scope of this disclosure.

Figure 17:
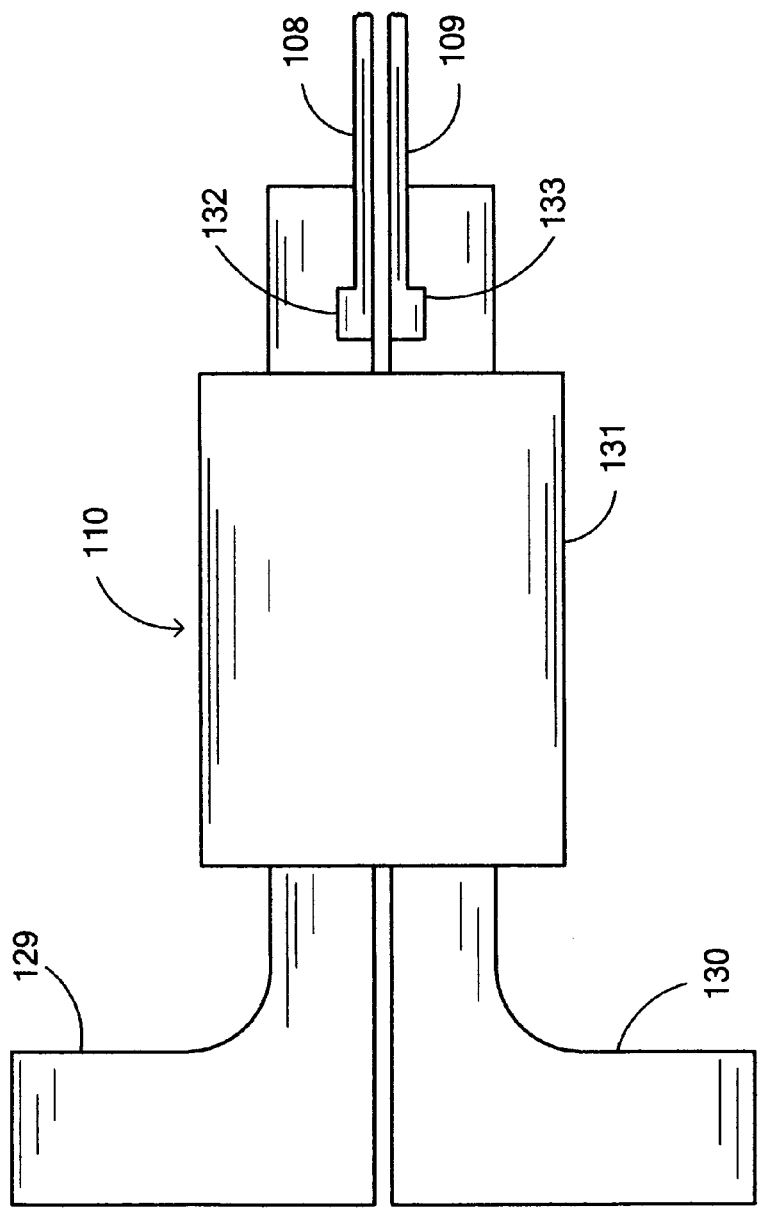
FIG. 17 is an expanded side view of a control mechanism at the proximal end of the apparatus of FIG. 2A, constructed in accordance with one embodiment of the present invention, the mechanism providing a means to grasp the apparatus and control the relative positions of the stylets.

Movement of the stylets may, for example, be controlled simply by directly grasping small plastic knobs attached to the proximal ends of each of the stylets, or preferably by use of a control mechanism. FIG. 17 is an expanded side view of a preferred embodiment of control mechanism 110 at the proximal end of apparatus 107. The control mechanism provides a convenient means to grasp apparatus 107 during insertion of the stylets into the lead and during the application of traction forces for lead extraction. The control mechanism also provides a convenient means to effect the relative longitudinal movement of the stylets, and precisely control the relative position of the stylets, which is required for expansion of the assembly. Radial expansion requires only a short distance of displacement of the stylets relative to each other, the extent of which is determined by the size and shape of the dimensional features dekribed above. This relative displacement may be achieved, for example in a preferred embodiment comprising 2 stylets, by moving the 2 stylets in opposite longitudinal directions or by moving one stylet while holding the other in a fixed position. In FIG. 17, control mechanism 110 comprises handles 129 and 130 and hollow cylinder 131 that are made of metal, molded plastic or other suitable material, and are large enough to manipulate manually. Handle 129 is attached to the proximal end of stylet 108 and handle 130 is attached to the proximal end of stylet 109. The distal portions of handles 129 and 130 are surrounded by and held together by hollow cylinder 131, but move within the cylinder. In a preferred embodiment, control mechanism 110 incorporates a locking feature. This feature allows the handles to move freely within the cylinder during expansion of the stylet assembly, but prevents relative movement of the stylets during insertion into the lead and during application of traction forces. This may be accomplished, for example, by making the distal portions of handles 129 and 130 cylindrical on their outer surfaces and flat on their adjacent sides, and by making cylinder 131 slightly elliptical rather than round. In this case, as cylinder 131 is rotated out of alignment with respect to handles 129 and 130, the cylinder tightens around the handles preventing further relative movement of the stylets.

In another embodiment of control mechanism 110, knobs on the proximal ends of stylets 108 and 109 are housed within cavities in the body of the control mechanism. As each knob is advanced or retracted within the control mechanism, the corresponding stylet is advanced or retracted. The movement of each knob may be controlled for example by a screw mechanism. Alternatively, the relative movement of the stylets may be controlled by a lever mechanism that advances or retracts each stylet to achieve the desired position.

Other mechanical methods may also be used similarly within control mechanism 110 to control the relative movement of the stylets, without departing from the scope of this disclosure.

In a preferred embodiment, control mechanism 110 is constructed to be removable from stylets 108 and 109, to allow excising extraction sheaths to be advanced over the lead body or to make the control mechanism reusable with other stylets. This may be accomplished, for example, by molding handles 129 and 130 with slots 132 and 133 into which the proximal ends of the stylets are placed but not permanently attached. Alternatively, in other embodiments it may be advantageous to permanently attach control mechanism 110 to the stylet assembly. This may be accomplished, for example, by molding and permanently attaching the distal ends of handles 129 and 130 around the proximal ends of the respective stylets.

In the embodiments discussed above, the assembly comprised 2 stylets. The concepts of this disclosure are applicable to assemblies comprising more than 2 stylets that are constructed and used similarly to those described above. As the number of mated stylets is increased, expansion of the assembly occurs radially in more directions, providing more evenly distributed engagement forces to facilitate lead extraction. However, it should be apparent that the complexity associated with more than 2 stylets increases the difficulty of manufacture and usage. Because the typical diameter of the coil lumen in conventional leads is small, the number of stylets comprising the assembly is also limited by material properties and limitations of machining technology. As an example, the apparatus may comprise 3 similar stylets and a control mechanism. As was the case for the embodiments utilizing 2 stylets, dimensional features on the adjacent sides of each of the 3 stylets mate together to achieve a minimum overall assembly diameter during advancement into the lead body. As explained above, relative longitudinal movement of the stylets results in radial expansion of the assembly. The concepts discussed above related to feature shape, feature placement, lubricious and adhesive coatings, enhancements for temporarily maintaining the relative position of the stylets, and control mechanisms are equally applicable for assemblies comprising more than 2 stylets.

In the embodiments discussed above, an electrical lead is used as an example for the implanted structure to be removed. However, the concept of the apparatus and method of use of this disclosure are applicable to the removal of other flexible, elongated implanted structures that contain an internal lumen. In addition, if access exists to multiple lumens in an implanted structure, multiple stylet assemblies could be used simultaneously to facilitate the extraction process. As an example of a different structure, an implantable catheter may be used for drug or fluid delivery to a location in the body that is remote from the reservoir. The catheter may be constructed of a flexible material such as silicone or polyurethane, similar to the electrical leads described above, and have an open internal lumen, but would not necessarily include an internal metal coil. The catheter may be one that is implanted transvenously or subcutaneously, similarly to the electrical leads described above. The apparatus and method of use described above for removal of an implanted lead apply equally well to the removal of this type of catheter. In this case, stylets 108 and 109 of apparatus 107 are inserted into the lumen of the catheter. Interaction of dimensional features 111 and 112 of the stylets, during relative longitudinal movement, results in radial expansion of the assembly, engaging the luminal surface of the catheter and allowing for the application of traction forces during catheter extraction. All the embodiments and concepts for the apparatus and method of use that are discussed above, related to feature shape, feature placement, lubricious and adhesive coatings, enhancements for temporarily maintaining the relative position of the stylets, control mechanisms, and number of stylets, are equally applicable to this situation.

What is claimed is:

1. An apparatus for structurally reinforcing and stabilizing the components of an implanted transvenous lead having an internal coil with a lumen during extraction from a body, said apparatus comprising:
    (a) a first wire stylet comprising a solid, substantially cylindrical wire with a distinct first side having a contour characterized by a sloped geometric pattern extending over the full width of the wire stylet and providing varying wire thickness along a portion of the length of said first wire stylet;
    (b) a second wire stylet comprising a solid, substantially cylindrical wire with a distinct first side having a contour characterized by a sloped geometric pattern extending over the full width of the wire stylet and providing varying wire thickness along a portion of the length of said second wire stylet; and
    (c) a flexible, close-fitting sheath around said first and second wire stylets for temporarily holding said wire stylets adjacently together along their lengths prior to insertion, said sheath being progressively removable during insertion of said wire stylets into the lumen of the implanted lead;
    (d) said first wire stylet and said second wire stylet being mechanically unattached to each other along their distal portions and being independently slideable, relative to each other along their entire lengths, longitudinally from a first position to a second position when said first side of said first wire stylet and said first side of said second wire stylet are placed contiguous, and said first wire stylet and said second wire stylet are inserted into the lumen of the implanted lead;
    (e) said contour of said first side of said first wire stylet being matched to and mating with said contour of said first side of said second wire stylet, allowing the combination of said first wire stylet and said second wire stylet to have a minimal diameter when in said first position relative to each other, and causing radial expansion of the combination by interaction of opposing, contoured contacting surfaces when said first wire stylet and said second wire stylet are moved relative to each other in a longitudinal direction to said second position; and
    (f) said combination of said first wire stylet and said second wire stylet having an overall diameter between 0.2 mm and 2.0 mm when in said first position, to permit insertion into the lumen of the implanted lead and large enough to exert sufficient pressure against the surface of the lumen to allow traction forces to be applied when in said second position,
    whereby the implanted lead may be removed from the body through the application of traction forces, while deformation is minimized and the structural integrity of the implanted lead is maintained.

2. The apparatus of claim 1 wherein said dimensional features cause radial expansion of said assembly in a direction parallel to a plane introduced between the adjacent sides of said wire stylets.

3. The apparatus of claim 1, further including a manual control mechanism, said control mechanism comprising a cylindrical handle attached to said wire stylets at a proximal end of said apparatus for manually effecting movement of said first wire stylet and said second wire stylet relative to each other, for manually controlling the longitudinal positions of said first wire stylet and said second wire stylet within the lumen of the implanted lead and for providing a traction force.

4. An apparatus that facilitates removal, from a body, of a transvenous lead having an internal coil with a lumen, said apparatus comprising 2 similar wire stylets and a flexible, removable sheath:

said wire stylets each comprising a solid wire with a substantially cylindrical shape and having as one side of the stylet's length a distinct geometric ruled surface having dimensional features, said dimensional features characterized by oscillating high and low regions of wire thickness and by a shape allowing said dimensional features to mate with matched, corresponding dimensional features of the adjacent wire stylet;

said wire stylets, being separate and without physical connection to each other along their distal portions, together forming an assembly for insertion into the lumen of the implanted lead coil, when placed contiguously with a cylindrical surface of each said wire stylet positioned to be adjacent to the luminal surface of the implanted lead coil and said geometric ruled surface with dimensional features positioned to be a central, contiguous side between said stylets;

said dimensional features having sloped mating surfaces extending uniformly across the full width of said ruled surface, allowing said assembly to have a minimal overall diameter when said wire stylets are in a first position relative to each other, and causing radial expansion of said assembly by interaction of opposing, contacting sloped surfaces when said wire stylets are moved longitudinally to a second position relative to each other;

said sheath being a flexible, close-fitting covering around said assembly of wire stylets for temporarily holding said wire stylets adjacently together along their lengths prior to insertion, and being progressively removable during insertion of said wire stylets into the lumen of the implanted lead coil;

said wire stylets being movable together in a longitudinal direction within the lumen of the implanted lead coil, as a result of manipulation at a proximal end of said apparatus;

said wire stylets being separate and movable independently in a longitudinal direction along their entire lengths from said first position to said second position relative to each other, within the lumen of the implanted lead coil, as a result of manipulation at the proximal end of said apparatus; and said assembly of said wire stylets having an overall diameter between 0.2 mm and 2.0 mm when in said first position to permit insertion into the lumen of the implanted lead coil, and large enough when in said second position to exert sufficient pressure to engage the luminal surface of the lead coil, whereby the implanted transvenous lead may be removed from the body through the application of traction forces, while the structural integrity of the implanted lead is maintained.

5. The apparatus of claim 4 wherein said dimensional features are located along substantially the entire length of said wire stylets.

6. The apparatus of claim 4 wherein said dimensional features are located periodically along the length of said wire stylets.

7. The apparatus of claim 4 wherein said dimensional features are located only at a distal end of said wire stylets.

8. The apparatus of claim 4 wherein said dimensional features have a rounded, oscillating profile.

9. The apparatus of claim 4 wherein said dimensional features have a linear, sawtooth shape profile.

10. The apparatus of claim 4 wherein contours of the dimensional features are asymmetrical, whereby the rate of radial expansion is dependent on the direction of relative longitudinal movement of said wire stylets.

11. The apparatus of claim 4, further including means on the outer surfaces of said wire stylets to increase frictional contact with the lumen of the implanted lead coil when said assembly is in said second position, of expanded radial dimension.

12. The apparatus of claim 4, further including means on the outer surfaces of said wire stylets to decrease frictional contact with the lumen of the implanted lead coil when said assembly is in said first position, of minimal diameter.

13. The apparatus of claim 4, further including means on the adjacent surfaces of said wire stylets to decrease frictional contact between said wire stylets.

14. The apparatus of claim 4, further including a manual control mechanism, said control mechanism comprising a cylindrical handle attached to said wire stylets at the proximal end of said apparatus for manually effecting movement of said wire stylets relative to each other and for manually controlling the longitudinal positions of said wire stylets within the lumen of the implanted lead.

15. The apparatus of claim 14 wherein said handle for controlling the relative position of said stylets is permanently attached to said stylets.

16. The apparatus of claim 14 wherein said handle for controlling the relative position of said stylets is removable.

17. The apparatus of claim 4 wherein said dimensional features cause radial expansion of said assembly in a direction perpendicular to a plane introduced between the adjacent sides of said wire stylets.

18. A method facilitating removal from a body, of a transvenous lead having an internal coil with a lumen, comprising:

(a) providing an apparatus comprising 2 similar wire stylets and a flexible, removable sheath:

said wire stylets each comprising a solid wire with a substantially cylindrical shape and having as one side of the stylet's length a distinct geometric ruled surface having dimensional features, said dimensional features characterized by oscillating high and low regions of wire thickness and by a shape allowing said dimensional features to mate with matched, corresponding dimensional features of the adjacent wire stylet;

said wire stylets, being separate and without physical connection to each other along their distal portions, together forming an assembly for insertion into the lumen of the implanted lead coil, when placed contiguously with a cylindrical surface of each said wire stylet positioned to be adjacent to the luminal surface of the implanted lead coil and said geometric ruled surface with dimensional features positioned to be a central, contiguous side between said stylets;

said dimensional features having sloped mating surfaces extending uniformly across the full width of the ruled surface, allowing said assembly to have a minimal overall diameter when said wire stylets are in a first position relative to each other, and causing radial expansion of said assembly by interaction of opposing, contacting sloped surfaces when said wire stylets are moved longitudinally to a second position relative to each other;

said sheath being a flexible, close-fitting covering around said assembly of wire stylets for temporarily holding said wire stylets adjacently together along their lengths prior to insertion, and being progressively removable during insertion of said wire stylets into the lumen of the implanted lead coil;

said wire stylets being movable together in a longitudinal direction within the lumen of the implanted lead coil, as a result of manipulation at a proximal end of said apparatus;

said wire stylets being separate and movable independently in a longitudinal direction along their entire lengths from said first position to said second position relative to each other, within the lumen of the implanted lead coil, as a result of manipulation at the proximal end of said apparatus; and said assembly of said wire stylets having an overall diameter between 0.2 mm and 2.0 mm when in said first position to permit insertion into the lumen of the implanted lead coil, and large enough when in said second position to exert sufficient pressure to engage the luminal surface of the lead coil;

(b) inserting said apparatus into the lumen of the lead coil to a desired depth, while said stylet assembly is in said first position of minimal diameter; and (c) moving said wire stylets relative to each other in a longitudinal direction from said first position of minimal diameter to said second position of expanded diameter, whereby radial forces engage the implanted lead and traction forces may be applied to remove the structure from the body, while the structural integrity of the implanted structure is maintained.

19. The method of claim 18 further comprising:

(d) moving said wire stylets relative to each other in a longitudinal direction from said second position of expanded diameter to said first position of minimal diameter;

(e) repositioning said assembly of said wire stylets within the lumen of the lead coil;

(f) moving said wire stylets relative to each other in a longitudinal direction from said first position of minimal diameter to said second position of expanded diameter.

* * * * *